(12) United States Patent
Mueller et al.

(10) Patent No.: US 7,544,208 B1
(45) Date of Patent: Jun. 9, 2009

(54) ADJUSTABLE CORPECTOMY APPARATUS

(75) Inventors: Richard Mueller, Macedonia, OH (US); Andrew Budd, Uniontown, OH (US)

(73) Assignee: Theken Spine, LLC, Akron, OH (US)

( * ) Notice: Subject to any disclaimer, the term of this patent is extended or adjusted under 35 U.S.C. 154(b) by 87 days.

(21) Appl. No.: 11/120,034

(22) Filed: May 2, 2005

Related U.S. Application Data (60) Provisional application No. 60/567,619, filed on May 3, 2004, provisional application No. 60/567,618, filed on May 3, 2004, provisional application No. 60/567,667, filed on May 3, 2004, provisional application No. 60/567,554, filed on May 3, 2004, provisional application No. 60/567,555, filed on May 3, 2004, provisional application No. 60/567,556, filed on May 3, 2004, provisional application No. 60/567,564, filed on May 3, 2004.

(51) Int. Cl.
*A61F 2/44* (2006.01)

(52) U.S. Cl. .................................... 623/17.15

(58) Field of Classification Search ............ 623/17.11, 623/17.15, 17.16; 403/109.2, 109.8; 254/2 B, 254/7 B, 7 R, 93 H, 98, 133 R, 134
See application file for complete search history.

(56) References Cited

U.S. PATENT DOCUMENTS

| | | | |
|---|---|---|---|
| 2,677,369 A | 5/1954 | Knowles |
| 3,307,505 A | 3/1967 | Windross |
| 3,745,995 A | 7/1973 | Kraus |
| 3,774,244 A | 11/1973 | Walker |
| 3,848,601 A | 11/1974 | Ma et al. |
| 3,855,638 A | 12/1974 | Pilliar |
| 3,867,728 A | 2/1975 | Stubstad et al. |
| 3,894,467 A | 7/1975 | Brescia |
| 3,906,550 A | 9/1975 | Rostoker et al. |
| 4,026,304 A | 5/1977 | Levy |
| 4,285,071 A | 8/1981 | Nelson et al. |
| 4,309,777 A | 1/1982 | Patil |
| 4,349,921 A | 9/1982 | Kuntz |
| 4,429,691 A | 2/1984 | Niwa et al. |

(Continued)

FOREIGN PATENT DOCUMENTS

CA    2088066    1/1992

(Continued)

*Primary Examiner*—Thomas C Barrett
*Assistant Examiner*—Nicholas Woodall
(74) *Attorney, Agent, or Firm*—Middleton Reutlinger; Robert H. Eichenberger; Eric L. Killmeier (57) ABSTRACT

A spinal fixation apparatus comprising an upper and lower endplate. Depending distally in a longitudinal direction from the upper endplate is an inner sleeve that fits inside an outer sleeve that depends distally in a longitudinal direction from the lower endplate. The inner sleeve includes grooves located on its outer surface. A finger cage including resilient fingers fits around the outer sleeve. The fingers have ends that include male grooves. The ends of the fingers fit into apertures located in the outer sleeve. The apparatus further includes a locking mechanism that pushes the tips of the fingers through the apertures of the outer sleeve such that they mesh with the grooves of the inner sleeve. When the locking mechanism is unlocked the tips of the fingers disengage from the grooves of the inner sleeve, and the inner sleeve slide axially within the outer cage, adjusting the height of the device.

16 Claims, 9 Drawing Sheets

U.S. PATENT DOCUMENTS

| | | |
|---|---|---|
| 4,484,570 A | 11/1984 | Sutter et al. |
| 4,501,269 A | 2/1985 | Bagby |
| 4,542,539 A | 9/1985 | Rowe, Jr. et al. |
| 4,553,273 A | 11/1985 | Wu |
| 4,554,914 A | 11/1985 | Kapp et al. |
| 4,563,778 A | 1/1986 | Roche et al. |
| 4,657,550 A | 4/1987 | Daher |
| 4,693,721 A | 9/1987 | Ducheyne |
| 4,714,469 A | 12/1987 | Kenna |
| 4,736,738 A | 4/1988 | Lipovsek et al. |
| 4,743,256 A | 5/1988 | Brantigan |
| 4,759,766 A | 7/1988 | Buettner-Janz et al. |
| 4,781,591 A | 11/1988 | Allen |
| 4,820,305 A | 4/1989 | Harms et al. |
| 4,834,757 A | 5/1989 | Brantigan |
| 4,877,020 A | 10/1989 | Vich |
| 4,878,915 A | 11/1989 | Brantigan |
| 4,892,546 A | 1/1990 | Kotz et al. |
| 4,932,975 A | 6/1990 | Main et al. |
| 4,938,768 A | 7/1990 | Wu |
| 4,946,378 A | 8/1990 | Hirayama et al. |
| 4,961,740 A | 10/1990 | Ray et al. |
| 5,026,373 A | 6/1991 | Ray et al. |
| 5,055,104 A | 10/1991 | Ray |
| 5,062,845 A | 11/1991 | Kuslich et al. |
| 5,071,437 A | 12/1991 | Steffee |
| 5,133,717 A | 7/1992 | Chopin |
| 5,147,402 A | 9/1992 | Bohler et al. |
| 5,171,278 A | 12/1992 | Pisharodi |
| 5,171,281 A | 12/1992 | Parsons et al. |
| 5,192,326 A | 3/1993 | Bao et al. |
| 5,192,327 A | 3/1993 | Brantigan |
| 5,201,766 A | 4/1993 | Georgette |
| 5,222,983 A | 6/1993 | Schmitz et al. |
| 5,236,460 A | 8/1993 | Barber |
| 5,250,061 A | 10/1993 | Michelson |
| 5,290,312 A | 3/1994 | Kojimoto et al. |
| 5,290,494 A | 3/1994 | Coombes et al. |
| 5,300,076 A | 4/1994 | Leriche |
| 5,304,210 A | 4/1994 | Crook |
| 5,306,307 A | 4/1994 | Senter et al. |
| 5,306,309 A | 4/1994 | Wagner et al. |
| 5,314,478 A | 5/1994 | Oka et al. |
| 5,330,535 A | 7/1994 | Moser et al. |
| 5,336,223 A | 8/1994 | Rogers |
| 5,364,400 A | 11/1994 | Rego, Jr. et al. |
| 5,390,683 A | 2/1995 | Pisharodi |
| 5,395,372 A | 3/1995 | Holt et al. |
| 5,397,364 A | 3/1995 | Kozak et al. |
| 5,405,391 A | 4/1995 | Hednerson et al. |
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,445,639 A | 8/1995 | Kuslich et al. |
| 5,454,811 A | 10/1995 | Huebner |
| 5,458,638 A | 10/1995 | Kuslich et al. |
| 5,458,643 A | 10/1995 | Oka et al. |
| 5,489,308 A | 2/1996 | Kuslich et al. |
| 5,514,180 A | 5/1996 | Heggeness et al. |
| 5,522,879 A | 6/1996 | Scopelianos |
| 5,522,899 A | 6/1996 | Michelson |
| 5,524,624 A | 6/1996 | Tepper et al. |
| 5,534,030 A | 7/1996 | Navarro et al. |
| 5,545,229 A | 8/1996 | Parsons et al. |
| 5,549,679 A | 8/1996 | Kuslich |
| 5,562,736 A | 10/1996 | Ray et al. |
| 5,562,738 A | 10/1996 | Boyd et al. |
| 5,565,005 A | 10/1996 | Erickson et al. |
| 5,571,190 A | 11/1996 | Ulrich et al. |
| 5,571,192 A | 11/1996 | Schonhoffer |
| 5,582,612 A | 12/1996 | Lin |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,609,637 A | 3/1997 | Biedermann et al. |
| 5,645,598 A | 7/1997 | Brosnahan, III |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs et al. |
| 5,664,762 A * | 9/1997 | Rothbauer .................. 254/103 |
| 5,665,089 A | 9/1997 | Dall et al. |
| 5,665,119 A | 9/1997 | Koller |
| 5,665,122 A | 9/1997 | Kambin |
| 5,669,909 A | 9/1997 | Zdeblick et al. |
| 5,674,294 A | 10/1997 | Bainville et al. |
| 5,683,393 A | 11/1997 | Ralph |
| 5,683,394 A | 11/1997 | Rinner |
| 5,683,464 A | 11/1997 | Wagner et al. |
| 5,700,264 A | 12/1997 | Zucherman et al. |
| 5,700,291 A | 12/1997 | Kuslich et al. |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,711,957 A | 1/1998 | Patat et al. |
| 5,716,415 A | 2/1998 | Steffee |
| 5,723,013 A | 3/1998 | Jeanson et al. |
| 5,749,916 A | 5/1998 | Richelsoph |
| 5,766,176 A | 6/1998 | Duncan |
| 5,766,252 A | 6/1998 | Henry et al. |
| 5,766,253 A | 6/1998 | Brosnahan |
| 5,772,661 A | 6/1998 | Michelson |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,782,830 A | 7/1998 | Farris |
| 5,782,832 A | 7/1998 | Larsen et al. |
| 5,782,919 A | 7/1998 | Zdeblick et al. |
| 5,785,710 A | 7/1998 | Michelson |
| 5,797,909 A | 8/1998 | Michelson |
| 5,800,547 A | 9/1998 | Schafer et al. |
| 5,800,549 A | 9/1998 | Bao et al. |
| 5,800,550 A | 9/1998 | Sertich |
| 5,814,048 A | 9/1998 | Morgan |
| 5,814,084 A | 9/1998 | Grivas et al. |
| D403,069 S | 12/1998 | Drewry et al. |
| 5,865,845 A | 2/1999 | Thalgott |
| 5,865,848 A | 2/1999 | Baker |
| 5,885,299 A | 3/1999 | Winslow et al. |
| 5,888,222 A | 3/1999 | Coates et al. |
| 5,888,224 A | 3/1999 | Beckers et al. |
| 5,888,227 A | 3/1999 | Cottle |
| 5,893,890 A | 4/1999 | Pisharodi |
| 5,897,556 A | 4/1999 | Drewry et al. |
| 5,904,719 A | 5/1999 | Errico et al. |
| 5,910,315 A | 6/1999 | Stevenson et al. |
| 5,913,860 A | 6/1999 | Scholl |
| 5,951,556 A | 9/1999 | Faccioli et al. |
| 5,957,836 A | 9/1999 | Johnson |
| 5,961,554 A | 10/1999 | Janson et al. |
| 5,968,062 A | 10/1999 | Thomas et al. |
| 5,968,098 A | 10/1999 | Winslow |
| 5,972,031 A | 10/1999 | Biedermann et al. |
| 5,980,540 A | 11/1999 | Bruce |
| 5,989,289 A | 11/1999 | Coates et al. |
| 5,989,290 A | 11/1999 | Biedermann et al. |
| 6,004,326 A | 12/1999 | Castro et al. |
| 6,015,436 A * | 1/2000 | Schonhoffer .............. 623/17.16 |
| 6,015,439 A | 1/2000 | Schonhoffer |

| Patent No. | Kind | Date | Inventor |
|---|---|---|---|
| 6,019,793 | A | 2/2000 | Perren et al. |
| 6,033,405 | A | 3/2000 | Winslow et al. |
| 6,039,762 | A | 3/2000 | McKay |
| 6,045,579 | A | 4/2000 | Hochshuler et al. |
| 6,059,829 | A | 5/2000 | Schlapfer et al. |
| 6,063,088 | A | 5/2000 | Winslow |
| 6,066,175 | A | 5/2000 | Henderson et al. |
| 6,074,423 | A | 6/2000 | Lawson |
| 6,080,155 | A | 6/2000 | Michelson |
| 6,080,193 | A | 6/2000 | Hochshuler et al. |
| 6,083,225 | A | 7/2000 | Winslow et al. |
| 6,086,613 | A | 7/2000 | Camino et al. |
| 6,090,143 | A | 7/2000 | Meriwether et al. |
| 6,093,205 | A | 7/2000 | McLeod et al. |
| 6,093,207 | A | 7/2000 | Pisharodi |
| 6,096,038 | A | 8/2000 | Michelson |
| 6,099,483 | A | 8/2000 | Palmer et al. |
| 6,102,948 | A | 8/2000 | Brosnahan, III |
| 6,102,950 | A | 8/2000 | Vaccaro |
| 6,106,557 | A | 8/2000 | Robioneck et al. |
| 6,113,638 | A | 9/2000 | Williams et al. |
| 6,120,503 | A | 9/2000 | Michelson |
| 6,120,506 | A | 9/2000 | Kohrs et al. |
| 6,123,705 | A | 9/2000 | Michelson |
| 6,126,660 | A | 10/2000 | Dietz |
| 6,136,031 | A | 10/2000 | Middleton |
| 6,143,032 | A | 11/2000 | Schafer et al. |
| 6,143,033 | A | 11/2000 | Paul et al. |
| 6,149,651 | A | 11/2000 | Drewry et al. |
| 6,159,211 | A | 12/2000 | Boriani et al. |
| 6,159,244 | A | 12/2000 | Suddaby |
| 6,174,311 | B1 | 1/2001 | Branch et al. |
| 6,174,334 | B1 | 1/2001 | Suddaby |
| 6,176,881 | B1 * | 1/2001 | Schar et al. ............... 623/17.11 |
| 6,190,413 | B1 | 2/2001 | Sutcliffe |
| 6,193,755 | B1 | 2/2001 | Metz-Stavenhagen et al. |
| 6,193,756 | B1 | 2/2001 | Studer et al. |
| 6,200,348 | B1 | 3/2001 | Biedermann et al. |
| 6,206,924 | B1 | 3/2001 | Timm |
| 6,224,595 | B1 | 5/2001 | Michelson |
| 6,238,397 | B1 | 5/2001 | Zucherman et al. |
| 6,241,729 | B1 | 6/2001 | Estes et al. |
| 6,245,072 | B1 | 6/2001 | Zdeblick et al. |
| 6,245,108 | B1 | 6/2001 | Biscup |
| 6,248,104 | B1 | 6/2001 | Chopin et al. |
| 6,258,125 | B1 | 7/2001 | Paul et al. |
| 6,283,967 | B1 | 9/2001 | Troxell et al. |
| 6,290,724 | B1 | 9/2001 | Marino |
| 6,296,665 | B1 | 10/2001 | Strnad et al. |
| 6,302,882 | B1 | 10/2001 | Lin et al. |
| D450,121 | S | 11/2001 | Anderson |
| 6,315,797 | B1 | 11/2001 | Middleton |
| 6,325,827 | B1 | 12/2001 | Lin |
| 6,332,895 | B1 | 12/2001 | Suddaby |
| 6,344,057 | B1 | 2/2002 | Rabbe et al. |
| 6,371,988 | B1 | 4/2002 | Pafford et al. |
| 6,375,681 | B1 | 4/2002 | Truscott |
| 6,395,034 | B1 | 5/2002 | Suddaby |
| 6,395,035 | B2 | 5/2002 | Bresina et al. |
| 6,409,765 | B1 | 6/2002 | Bianchi et al. |
| 6,413,258 | B1 | 7/2002 | Bernhardt, Jr. |
| 6,425,920 | B1 | 7/2002 | Hamada |
| 6,428,544 | B1 | 8/2002 | Ralph et al. |
| 6,436,101 | B1 | 8/2002 | Hamada |
| 6,440,142 | B1 | 8/2002 | Ralph et al. |
| 6,443,987 | B1 | 9/2002 | Bryan |
| 6,454,805 | B1 | 9/2002 | Baccelli et al. |
| 6,454,806 | B1 * | 9/2002 | Cohen et al. ............... 623/17.15 |
| 6,458,159 | B1 | 10/2002 | Thalgott |
| 6,468,311 | B2 | 10/2002 | Boyd et al. |
| 6,471,724 | B2 | 10/2002 | Zdeblick et al. |
| 6,471,958 | B2 | 10/2002 | Dimitrijevich et al. |
| 6,478,801 | B1 | 11/2002 | Ralph et al. |
| 6,478,823 | B1 | 11/2002 | Michelson |
| 6,494,883 | B1 | 12/2002 | Ferree |
| 6,500,205 | B1 | 12/2002 | Michelson |
| 6,500,206 | B1 | 12/2002 | Bryan |
| 6,520,192 | B1 * | 2/2003 | Lo ............... 135/25.4 |
| 6,520,996 | B1 | 2/2003 | Manasas et al. |
| 6,524,318 | B1 | 2/2003 | Longhini et al. |
| 6,524,341 | B2 * | 2/2003 | Lang et al. ............... 623/17.15 |
| 6,537,320 | B1 | 3/2003 | Michelson |
| 6,544,265 | B2 | 4/2003 | Lieberman |
| 6,562,074 | B2 | 5/2003 | Gerbec et al. |
| 6,565,574 | B2 | 5/2003 | Michelson |
| 6,575,981 | B1 | 6/2003 | Boyd et al. |
| 6,582,432 | B1 | 6/2003 | Michelson |
| 6,582,437 | B2 | 6/2003 | Dorchak et al. |
| 6,585,749 | B2 | 7/2003 | Hanson |
| 6,585,770 | B1 | 7/2003 | White et al. |
| 6,595,995 | B2 | 7/2003 | Zdeblick et al. |
| 6,607,557 | B1 | 8/2003 | Brosnahan et al. |
| 6,613,091 | B1 | 9/2003 | Zdeblick et al. |
| 6,616,671 | B2 | 9/2003 | Landry et al. |
| 6,645,206 | B1 | 11/2003 | Zdeblick et al. |
| 6,648,894 | B2 | 11/2003 | Abdelgany et al. |
| 6,648,895 | B2 | 11/2003 | Burkus et al. |
| 6,648,915 | B2 | 11/2003 | Sazy |
| 6,648,917 | B2 | 11/2003 | Gerbec et al. |
| 6,652,533 | B2 | 11/2003 | O'Neil |
| 6,652,584 | B2 | 11/2003 | Michelson |
| 6,660,038 | B2 | 12/2003 | Boyer, II et al. |
| 6,666,866 | B2 | 12/2003 | Martz et al. |
| 6,676,703 | B2 | 1/2004 | Biscup |
| 6,679,887 | B2 | 1/2004 | Nicholson et al. |
| 6,682,534 | B2 | 1/2004 | Patel et al. |
| 6,692,495 | B1 | 2/2004 | Zacouto |
| 6,699,288 | B2 | 3/2004 | Moret |
| 6,706,069 | B2 | 3/2004 | Berger |
| 6,709,458 | B2 | 3/2004 | Michelson |
| 6,712,819 | B2 | 3/2004 | Zucherman et al. |
| 6,712,852 | B1 | 3/2004 | Chung et al. |
| 6,716,247 | B2 | 4/2004 | Michelson |
| 6,719,760 | B2 | 4/2004 | Dorchak et al. |
| 6,719,794 | B2 | 4/2004 | Gerber et al. |
| 6,723,096 | B1 | 4/2004 | Dorchak et al. |
| 6,726,722 | B2 | 4/2004 | Walkenhorst et al. |
| 6,730,088 | B2 * | 5/2004 | Yeh ............... 606/61 |
| 6,730,127 | B2 | 5/2004 | Michelson |
| 6,733,533 | B1 | 5/2004 | Lozier |
| 6,733,534 | B2 | 5/2004 | Sherman |
| 6,733,535 | B2 | 5/2004 | Michelson |
| 6,740,091 | B2 | 5/2004 | Kohrs et al. |
| 6,743,232 | B2 | 6/2004 | Overaker et al. |
| 6,743,234 | B2 | 6/2004 | Burkus et al. |
| 6,746,454 | B2 | 6/2004 | Winterbottom et al. |
| 6,749,636 | B2 | 6/2004 | Michelson |
| 6,752,832 | B2 * | 6/2004 | Neumann ............... 623/17.15 |
| 6,755,841 | B2 | 6/2004 | Fraser et al. |
| 6,758,849 | B1 | 7/2004 | Michelson |
| 6,758,862 | B2 | 7/2004 | Berry et al. |
| 6,761,723 | B2 | 7/2004 | Buttermann et al. |
| 6,764,491 | B2 | 7/2004 | Frey et al. |
| 6,764,514 | B1 | 7/2004 | Li et al. |
| 6,776,798 | B2 | 8/2004 | Camino et al. |
| 6,783,547 | B2 | 8/2004 | Castro |
| RE38,614 | E | 10/2004 | Paul et al. |
| 6,802,867 | B2 | 10/2004 | Manasas et al. |
| 6,805,715 | B2 | 10/2004 | Reuter et al. |
| 6,808,538 | B2 | 10/2004 | Paponneau |
| 6,824,565 | B2 | 11/2004 | Muhanna et al. |
| 6,840,941 | B2 | 1/2005 | Rogers et al. |
| 6,843,804 | B2 | 1/2005 | Bryan |
| 6,852,129 | B2 | 2/2005 | Gerbec et al. |
| 6,855,166 | B2 | 2/2005 | Kohrs |
| 6,855,167 | B2 | 2/2005 | Shimp et al. |

| | | |
|---|---|---|
| 6,855,168 B2 | 2/2005 | Crozet |
| 6,863,673 B2 | 3/2005 | Gerbec et al. |
| 6,863,689 B2 | 3/2005 | Ralph et al. |
| 6,866,682 B1 * | 3/2005 | An et al. .................. 623/17.15 |
| 6,890,334 B2 | 5/2005 | Brace et al. |
| 6,890,355 B2 | 5/2005 | Michelson |
| 6,899,734 B2 | 5/2005 | Castro et al. |
| 6,902,566 B2 | 6/2005 | Zucherman et al. |
| 6,902,579 B2 | 6/2005 | Harms et al. |
| 6,908,485 B2 | 6/2005 | Crozet et al. |
| 6,923,810 B1 | 8/2005 | Michelson |
| 6,923,814 B1 | 8/2005 | Hildebrand et al. |
| 6,923,830 B2 | 8/2005 | Michelson |
| 6,929,662 B1 | 8/2005 | Messerli et al. |
| 6,981,975 B2 | 1/2006 | Michelson |
| 6,991,653 B2 | 1/2006 | White et al. |
| 6,991,654 B2 | 1/2006 | Foley |
| 6,997,953 B2 | 2/2006 | Chung et al. |
| 7,001,385 B2 | 2/2006 | Bonutti |
| 7,014,659 B2 | 3/2006 | Boyer, II et al. |
| 7,022,138 B2 | 4/2006 | Mashburn |
| 7,044,972 B2 | 5/2006 | Mathys, Jr. et al. |
| 7,056,343 B2 * | 6/2006 | Schafer et al. ........... 623/17.11 |
| 7,063,725 B2 | 6/2006 | Foley |
| 7,077,864 B2 | 7/2006 | Byrd, III et al. |
| 7,087,083 B2 | 8/2006 | Pasquet et al. |
| 7,128,762 B2 | 10/2006 | Middleton |
| 7,131,995 B2 | 11/2006 | Biedermann et al. |
| 7,135,025 B2 | 11/2006 | Pohjonen et al. |
| 7,135,042 B2 | 11/2006 | Stoll |
| 7,135,043 B2 | 11/2006 | Nakahara et al. |
| 7,137,997 B2 | 11/2006 | Paul |
| 7,141,068 B2 | 11/2006 | Ross et al. |
| 7,141,070 B2 | 11/2006 | Ralph et al. |
| 7,144,426 B2 | 12/2006 | Ralph et al. |
| 7,147,641 B2 | 12/2006 | Chen |
| 7,147,643 B2 | 12/2006 | Robioneck et al. |
| 7,153,304 B2 | 12/2006 | Robie et al. |
| 7,153,325 B2 | 12/2006 | Kim et al. |
| 7,156,858 B2 | 1/2007 | Schuldt-Hempe et al. |
| 7,156,874 B2 | 1/2007 | Paponneau et al. |
| 7,156,876 B2 | 1/2007 | Moumene et al. |
| 7,160,303 B2 | 1/2007 | Keller |
| 7,163,560 B2 | 1/2007 | Mason |
| 7,166,110 B2 | 1/2007 | Yundt |
| 7,166,129 B2 | 1/2007 | Michelson |
| 7,166,130 B2 | 1/2007 | Ferree |
| 7,166,131 B2 | 1/2007 | Studer et al. |
| 7,169,181 B2 | 1/2007 | Kuras |
| 7,169,182 B2 | 1/2007 | Errico et al. |
| 7,169,183 B2 | 1/2007 | Liu et al. |
| 7,172,595 B1 | 2/2007 | Goble |
| 7,172,628 B2 | 2/2007 | Lamprich et al. |
| 7,179,295 B2 | 2/2007 | Kovacevic |
| 7,179,299 B2 | 2/2007 | Edwards et al. |
| 7,182,781 B1 | 2/2007 | Bianchi et al. |
| 7,182,783 B2 | 2/2007 | Trieu |
| 7,182,784 B2 | 2/2007 | Evans et al. |
| 7,189,242 B2 | 3/2007 | Boyd et al. |
| 7,192,446 B2 | 3/2007 | Shapiro et al. |
| 7,192,447 B2 | 3/2007 | Rhoda |
| 7,195,643 B2 | 3/2007 | Jackson |
| 2001/0047208 A1 | 11/2001 | Michelson |
| 2002/0026196 A1 | 2/2002 | Simon |
| 2002/0028192 A1 | 3/2002 | Dimitrijevich et al. |
| 2002/0055782 A1 | 5/2002 | Bagby |
| 2002/0120274 A1 | 8/2002 | Overaker et al. |
| 2002/0143330 A1 | 10/2002 | Shluzas |
| 2002/0143400 A1 | 10/2002 | Biscup |
| 2002/0169448 A1 | 11/2002 | Vanacker |
| 2003/0018334 A1 | 1/2003 | Richelsoph et al. |
| 2003/0023306 A1 | 1/2003 | Liu et al. |
| 2003/0028192 A1 | 2/2003 | Schar et al. |
| 2003/0125739 A1 | 7/2003 | Bagga et al. |
| 2003/0167091 A1 | 9/2003 | Scharf |
| 2003/0167092 A1 | 9/2003 | Foley |
| 2003/0171813 A1 | 9/2003 | Kiester |
| 2003/0176925 A1 | 9/2003 | Paponneau |
| 2003/0176926 A1 | 9/2003 | Boehm, Jr. et al. |
| 2003/0181981 A1 | 9/2003 | Lemaire |
| 2003/0191531 A1 | 10/2003 | Berry et al. |
| 2003/0191535 A1 | 10/2003 | Castro |
| 2003/0195626 A1 | 10/2003 | Huppert |
| 2003/0195629 A1 | 10/2003 | Pafford et al. |
| 2003/0195632 A1 | 10/2003 | Foley et al. |
| 2003/0199983 A1 | 10/2003 | Michelson |
| 2004/0010315 A1 | 1/2004 | Song |
| 2004/0019356 A1 | 1/2004 | Fraser et al. |
| 2004/0030387 A1 | 2/2004 | Landry et al. |
| 2004/0034358 A1 | 2/2004 | Michelson |
| 2004/0034430 A1 | 2/2004 | Falahee |
| 2004/0049271 A1 | 3/2004 | Biedermann et al. |
| 2004/0054412 A1 | 3/2004 | Gerbec et al. |
| 2004/0059419 A1 | 3/2004 | Michelson |
| 2004/0059420 A1 | 3/2004 | Michelson |
| 2004/0064185 A1 | 4/2004 | Michelson |
| 2004/0068259 A1 | 4/2004 | Michelson |
| 2004/0078078 A1 | 4/2004 | Shepard |
| 2004/0078079 A1 | 4/2004 | Foley |
| 2004/0082999 A1 | 4/2004 | Mathys, Jr. et al. |
| 2004/0088054 A1 | 5/2004 | Berry |
| 2004/0093083 A1 | 5/2004 | Branch et al. |
| 2004/0093084 A1 | 5/2004 | Michelson |
| 2004/0093085 A1 | 5/2004 | Michelson |
| 2004/0093086 A1 | 5/2004 | Michelson |
| 2004/0097928 A1 | 5/2004 | Zdeblick et al. |
| 2004/0097929 A1 | 5/2004 | Branch et al. |
| 2004/0102848 A1 | 5/2004 | Michelson |
| 2004/0117017 A1 | 6/2004 | Pasquet et al. |
| 2004/0117018 A1 | 6/2004 | Michelson |
| 2004/0133280 A1 | 7/2004 | Trieu |
| 2004/0153160 A1 * | 8/2004 | Carrasco .................. 623/17.15 |
| 2004/0236427 A1 | 11/2004 | Berry et al. |
| 2005/0010294 A1 | 1/2005 | Michelson |
| 2005/0015097 A1 | 1/2005 | Mujwid et al. |
| 2005/0049706 A1 | 3/2005 | Brodke et al. |
| 2005/0090898 A1 * | 4/2005 | Berry et al. ............... 623/17.11 |
| 2005/0096745 A1 | 5/2005 | Andre et al. |
| 2005/0113921 A1 * | 5/2005 | An et al. .................. 623/17.11 |
| 2005/0131419 A1 | 6/2005 | McCord et al. |
| 2005/0159813 A1 | 7/2005 | Molz, IV |
| 2005/0216088 A1 | 9/2005 | McKinley et al. |
| 2005/0283236 A1 | 12/2005 | Razian |
| 2006/0058879 A1 | 3/2006 | Metz-Stavenhagen |
| 2006/0116770 A1 | 6/2006 | White et al. |

FOREIGN PATENT DOCUMENTS

| | | |
|---|---|---|
| CA | 2015507 | 1/1999 |
| DE | 2750648 | 5/1979 |
| DE | 3023942 | 1/1982 |
| DE | 3741487 | 6/1989 |
| DE | 4012622 | 7/1991 |
| DE | 4323595 | 7/1994 |
| DE | 19500170 | 2/1996 |
| DE | 19604246 | 8/1996 |
| DE | 19622827 | 12/1997 |
| EP | 0179695 | 4/1986 |
| EP | 0290767 | 11/1988 |
| EP | 0369603 | 10/1989 |
| EP | 0490159 | 11/1991 |
| EP | 0517030 | 5/1992 |
| EP | 0706876 | 9/1995 |
| EP | 0716840 | 12/1995 |
| EP | 1400221 | 6/1996 |
| EP | 0796593 | 3/1997 |

| | | | | | |
|---|---|---|---|---|---|
| EP | 0880938 | 5/1998 | WO | 9907312 | 2/1999 |
| EP | 1100417 | 2/2000 | WO | 9908627 | 2/1999 |
| EP | 1039855 | 10/2000 | WO | 9932055 | 7/1999 |
| EP | 1077659 | 2/2001 | WO | 9938461 | 8/1999 |
| EP | 1080703 | 3/2001 | WO | 9956675 | 11/1999 |
| EP | 1121075 | 8/2001 | WO | 0007527 | 2/2000 |
| EP | 1430857 | 12/2002 | WO | 0023013 | 4/2000 |
| EP | 1430858 | 12/2002 | WO | 0106962 | 2/2001 |
| EP | 1346709 | 3/2003 | WO | 0209786 | 2/2002 |
| EP | 1398008 | 7/2003 | WO | 0219952 | 3/2002 |
| EP | 1334703 | 8/2003 | WO | WO02/38086 | 5/2002 |
| EP | 1391188 | 8/2003 | WO | 02060356 | 8/2002 |
| EP | 1391189 | 8/2003 | WO | 02076335 | 10/2002 |
| EP | 1415622 | 9/2003 | WO | 02078514 | 10/2002 |
| EP | 1415623 | 9/2003 | WO | 03009786 | 2/2003 |
| EP | 1410770 | 4/2004 | WO | 03013399 | 2/2003 |
| JP | 2003/305068 | 10/2003 | WO | WO03/009786 | 2/2003 |
| JP | 2003305068 | 10/2003 | WO | WO03/013399 | 2/2003 |
| WO | 9106261 | 5/1991 | WO | 03020143 | 3/2003 |
| WO | 9201428 | 2/1992 | WO | 03026522 | 4/2003 |
| WO | 9404100 | 3/1994 | WO | 03026538 | 4/2003 |
| WO | 9418913 | 9/1994 | WO | 03068112 | 8/2003 |
| WO | 9501810 | 1/1995 | WO | 03096937 | 11/2003 |
| WO | 9608205 | 3/1996 | WO | WO03/096937 | 11/2003 |
| WO | 9640020 | 12/1996 | WO | 2004000177 | 12/2003 |
| WO | 9641582 | 12/1996 | WO | 2004008999 | 1/2004 |
| WO | 9733525 | 9/1997 | WO | 2004024038 | 3/2004 |
| WO | 9809586 | 3/1998 | WO | 2004026188 | 4/2004 |
| WO | 9814142 | 4/1998 | WO | 2004043306 | 5/2004 |
| WO | 9817208 | 4/1998 | WO | WO04/041130 | 5/2004 |
| WO | WO98/34552 | 8/1998 | WO | WO04/052245 | 6/2004 |
| WO | 9932054 | 1/1999 | | | |

* cited by examiner

ADJUSTABLE CORPECTOMY APPARATUS

CROSS REFERENCE TO RELATED APPLICATIONS

This application claims the benefit of U.S. Provisional Application Nos. 60/567,619 filed May 3, 2004; 60/567,618 filed May 3, 2004; 60,567,667 filed May 3, 2004; 60/567,554 filed May 3, 2004; 60/567,555 filed May 3, 2004; 60/567,556 filed May 3, 2004; 60/567,564 filed May 3, 2004; the entire disclosures of which are incorporated herein by reference.

BACKGROUND OF THE INVENTION

1. Field of the Invention

The present invention generally relates to the field of orthopaedic implants. Specifically, the present invention provides a prosthetic implant to replace spinal vertebra and adjacent intervertebral discs.

2. Background

The vertebral column serves as the main structural support of the human skeleton. The vertebral column consists of a number of vertebrae separated by intervertebral discs. A vertebra approximates a cylindrical shape, with wing-like projections and a bony arch. The arches create a passageway through which the spinal cord runs. The vertebral column is held upright by fibrous bands of muscle and ligament. There are seven vertebrae in the cervical region, twelve in the thoracic region, five in the lumbar region, and five in the sacral region that are usually fused together. The integrity of the vertebral column is critical to protecting the fragile spinal cord, in addition to its duties in supporting the skeleton.

When a vertebra or intervertebral disc becomes damaged, either through trauma or disease, the spinal cord or nerve roots may be impinged, causing a great deal of pain. This pain can occur almost anywhere in a person's body, from the back or neck to the extremities. In such a case, patients often receive drug treatment in an initial attempt to relieve the pain, but if that is unsuccessful, it may be necessary to remove all or a portion of one or more vertebrae, including the anterior cylindrical body, which is the load-bearing portion of intervertebral discs. When this procedure is undertaken, it necessarily weakens the support structure of the spinal column, and the excised material must be replaced with some load-bearing material. Given the high propensity of spinal discs to degenerate in human beings, the need for an efficient and stable method of spinal fixation is tremendous.

It is possible to replace the excised vertebral bone with a bone graft. The bone graft may be an autograft, normally harvested from the patient's iliac crest, or, alternatively, may be an allograft—tissue obtained from a human donor. Once the bone graft is in place spanning the bony defect, it fuses over time with the remaining healthy vertebrae. Generally, a metal plate and screws are used to secure the bone graft to the natural vertebrae, providing support until the fusion process is complete. However, given that it generally takes between three and six months for bony fusion to occur, a more substantive prosthetic implant is often used to stabilize the spine, often in combination with bone graft that can grow out of the prosthesis and fuse with the adjacent bone over time.

A prosthetic spinal fixation device should accurately replace the height of the excised material, result in acceptable tension levels in the spine, maintain proper curvature of the spine, obtain balance through the spinal segments, and restore normal load-bearing characteristics throughout the spine.

Moreover, a prosthetic spinal fixation device should be easily adjustable to allow the surgeon to quickly select the height of the device during surgery to fit the needs of the patient. The desired height of the device will depend on the amount of bone that is removed from the patient, the size of the patient, as well as the location of the removed bone (i.e. cervical region or lumbar region). In addition, a one-size-fits-all device may reduce manufacturing costs because fewer different parts and/or models will be required to meet the needs of the marketplace.

While prosthetic corpectomy implants are known in the art, a need exists for improved implants that are more easily adjusted to achieve the necessary height to replace the excised bone during the implantation process, while also possessing the biomechanical properties necessary for long-term implantation in the human body and the immediate fixation ability to provide stability to the spinal column.

BRIEF SUMMARY OF THE INVENTION

The present invention is directed to an artificial corpectomy prosthesis for replacement of one or more spinal vertebrae. The apparatus is adjustable in height through use of a lockable telescoping finger mechanism that allows a surgeon to choose the appropriate height for the prosthesis when performing the corpectomy procedure. The prosthesis comprises a first endplate and a second endplate; a substantially hollow outer member; a substantially hollow inner member; a fixation device; and a locking mechanism. The sleeves are also referred to herein as cages or substantially open cylinders. Either endplate can accommodate the outer sleeve. All that is required is that one sleeve fits inside the other sleeve in a cylindrical enveloping relationship and that the sleeves are moveable with respect to each other. For the sake of brevity and ease of description herein, the outer sleeve will be described as attaching to the second, or lower endplate. Once implanted, bone graft can be packed within slots inside the components of the device, and inside the inner member such that the bone graft can grow into the body and fuse with healthy bone adjacent the prosthesis.

The first and second endplates serve as the respective ends of the prosthesis, and fit against the healthy vertebrae adjacent to the removed vertebrae and vertebral discs. Each of the first and second endplates includes a first and a second surface.

The first surfaces of each endplate interact with the healthy bone adjacent each end of the prosthesis. One or both endplates may include a feature located on its first surface that encourages and/or facilitates fusion of the prosthesis and the healthy bone. This feature can be in the form of physical protuberances (such as spikes, ridges, keels, knurling, and the like) or chemical or biological treatments such as hydroxyapatite and the like. This improves the fixation characteristics of the prosthesis and lengthens the overall life of the prosthesis. The footprint and angle of the first surface of both the first and second endplates can be varied depending on the location of placement in the spine.

Depending distally in a longitudinal direction from the first endplate is an inner member. The inner member has an outer surface that comprises a number of circumferential grooves. The inner member can also include a number of holes or slots spaced longitudinally or radially along its outer surface.

Depending distally in a longitudinal direction from the second endplate is a substantially hollow outer member. The inside perimeter of the outer member is large enough that the inner member can fit within the hollow defined by the perimeter of the outer member. The outer member includes one or more locking apertures and preferably also includes one or more ingrowth apertures. When the inner member is inserted into the hollow of the outer member, the locking apertures provide access to the grooves present on the outer surface of the inner member.

A finger cage is a hollow body that fits over the outer member. The finger cage includes one or more resilient fingers that are free to bend inwardly or outwardly. The free end of each finger includes one or more tabs. When the finger cage is fitted in place over the outer member, the fingers of the finger cage align with the locking apertures of the outer member such that the tabs of the fingers are inserted through the locking apertures of the outer member and into engagement in the circumferential grooves of the inner member.

A locking mechanism comprises a ring that fits around the fingers of the finger cage. The locking mechanism preferably has two positions—locked and unlocked. When in the locked position, the tabs of the fingers are forced through the locking apertures of the finger cage and mesh with the grooves of the inner member. Which grooves of the inner member the tabs of the fingers engage depends upon how far the inner sleeve is inserted into the outer sleeve. Therefore, when the locking mechanism is in the locked position, the inner member is prevented from sliding axially with respect to the outer member, and the height of the apparatus is thus fixed.

When the locking mechanism is in the unlocked position, the tabs of the fingers are not forced to mesh with the grooves of the inner member, and the inner member is free to slide axially with respect to the outer member. Therefore, when the locking mechanism is in the unlocked position, the height of the apparatus may be adjusted by the surgeon to fit the needs of the individual patient by sliding the inner sleeve axially with respect to outer sleeve. Preferably, the fingers of the finger cage are resiliently biased in an outward direction. In this manner, the apparatus is adjustable at all times until the locking mechanism is moved into a locked position. Therefore, the grooves, the finger cage, and the locking ring comprise a means for selectively altering and fixing the height of the prosthesis.

If it is desired to prevent rotation of the inner member relative to the outer member, it is possible to incorporate a security mechanism between them to be activated after the desired height of the apparatus has been selected. The security mechanism could, as but one example, consist of a key inserted through a slot on the outer mechanism that is aligned with one of the slots or openings of the inner sleeve such that when the key is inserted, the inner sleeve is not free to rotate within the outer sleeve.

BRIEF DESCRIPTION OF THE DRAWINGS

The teachings of the present invention can be readily understood by considering the following detailed description of various exemplary embodiments in conjunction with the accompanying drawings, in which.

DETAILED DESCRIPTION OF THE PREFERRED EMBODIMENT

While the present invention will be described more fully hereinafter with reference to the accompanying drawings in which particular embodiments and methods are shown, it is to be understood from the outset that persons of ordinary skill in the art may modify the invention herein described while achieving the functions and results of this invention. Accordingly, the description that follows is to be understood as illustrative and exemplary of specific embodiments within the broad scope of the present invention and not as limiting the scope of the invention. In the following descriptions, like numbers refer to similar features or like elements throughout.

Ideally, an artificial corpectomy prosthetic provides the surgeon with an easy adjustment mechanism that allows the length of the prosthetic to be modified during surgery with a minimum of time and effort to fit the needs of the patient. The prosthetic must allow a significant range of adjustment because the size and number of vertebrae removed will vary from patient to patient.

Figure 1:
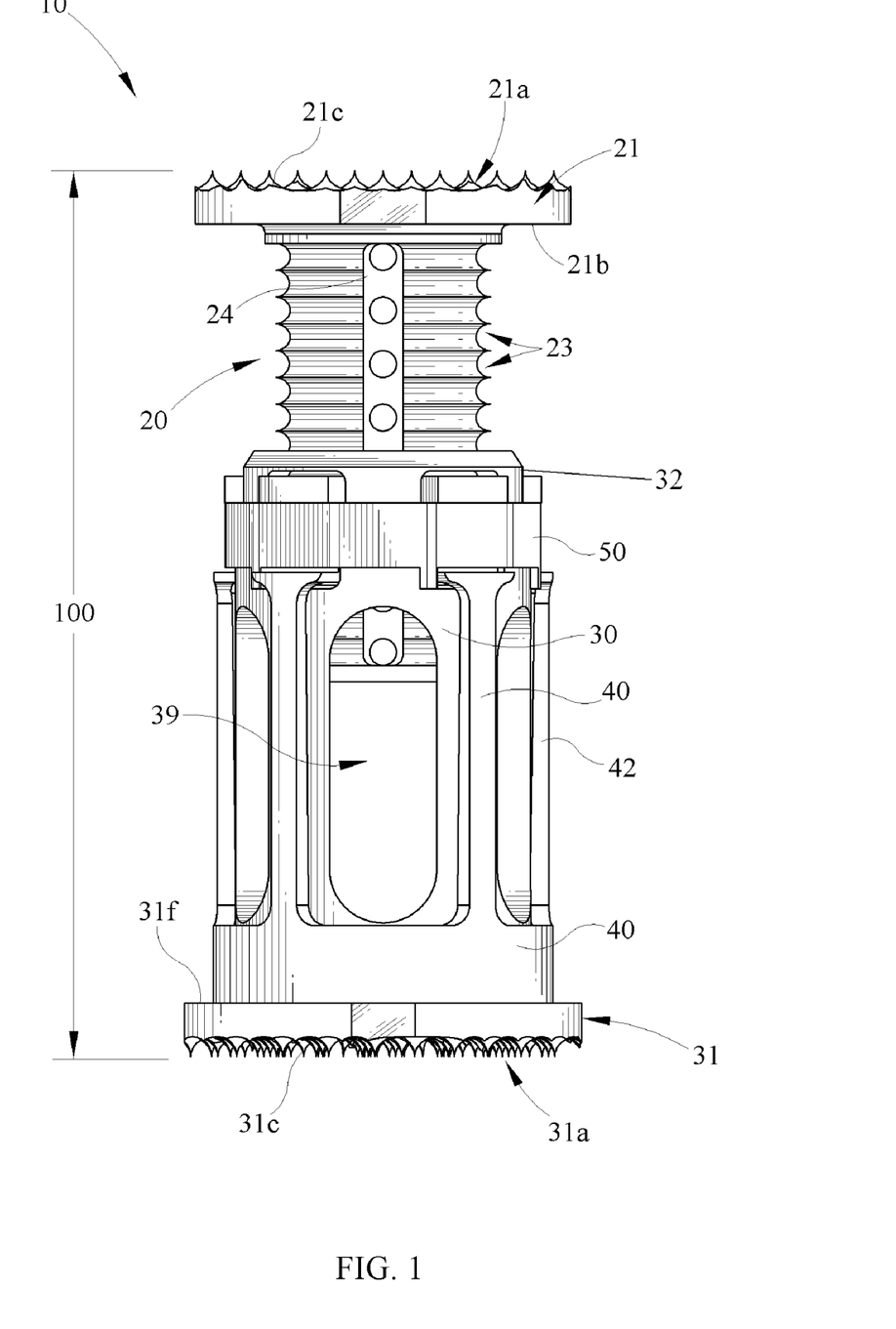
FIG. 1 is a side view of one embodiment of the present invention.

Referring now to FIG. 1, one embodiment of a prosthetic is shown which includes an adjustable telescoping mechanism that allows the height 100 of the prosthetic to be expanded or contracted during surgery, and also prevents both accidental compression or expansion of the device once implanted in the patient.

Figure 2:
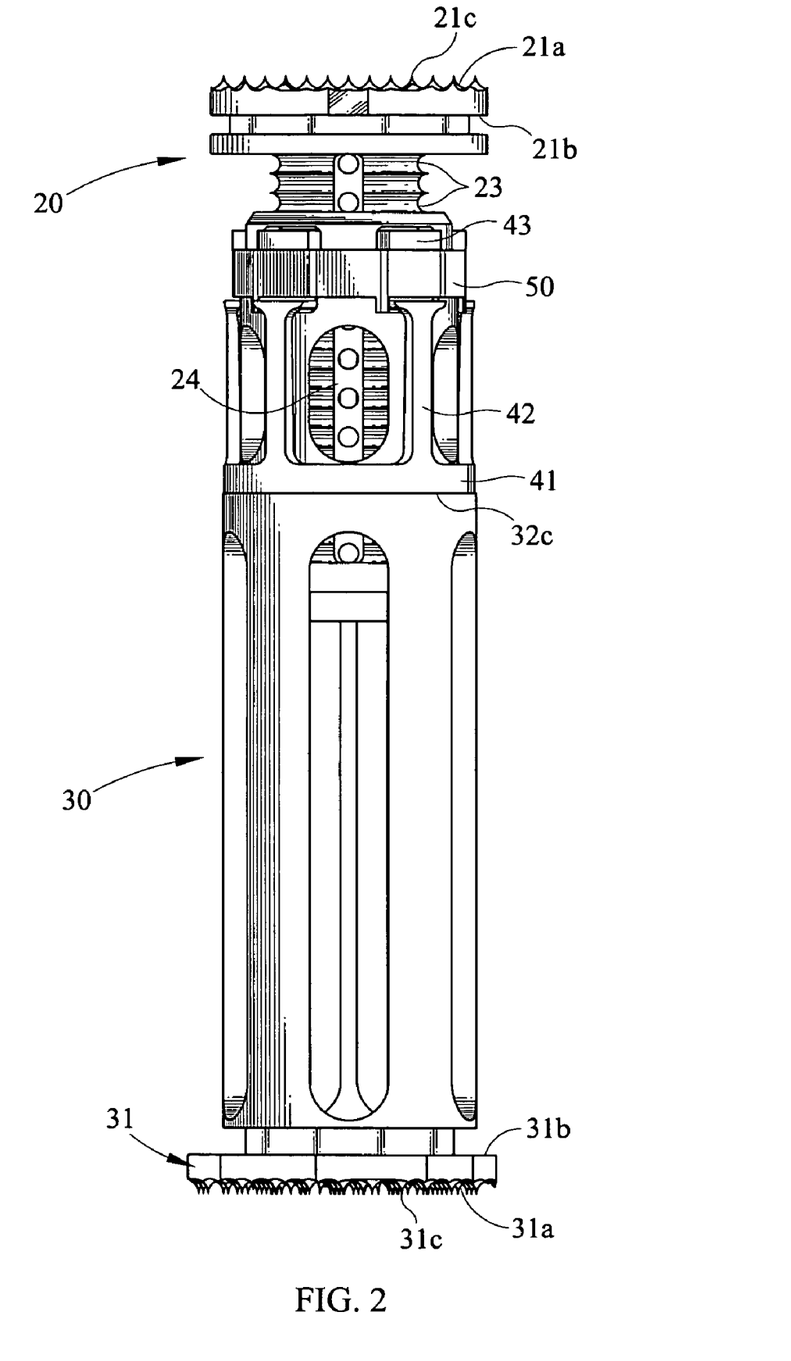
FIG. 2 is a side view of a second embodiment of the present invention.
Figure 4:
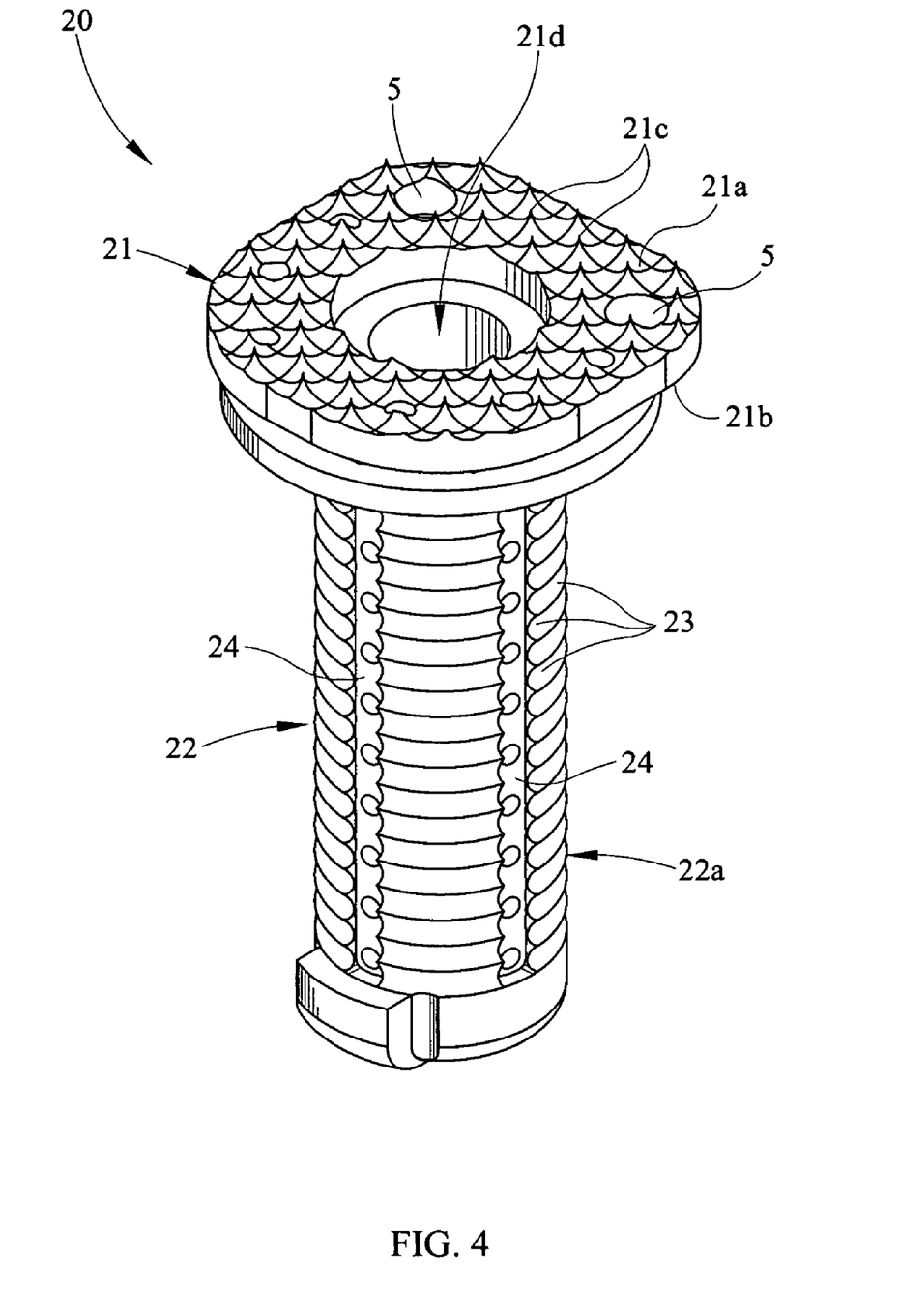
FIG. 4 is a partial perspective view depicting the inner member of one embodiment of the present invention.
Figure 4A:
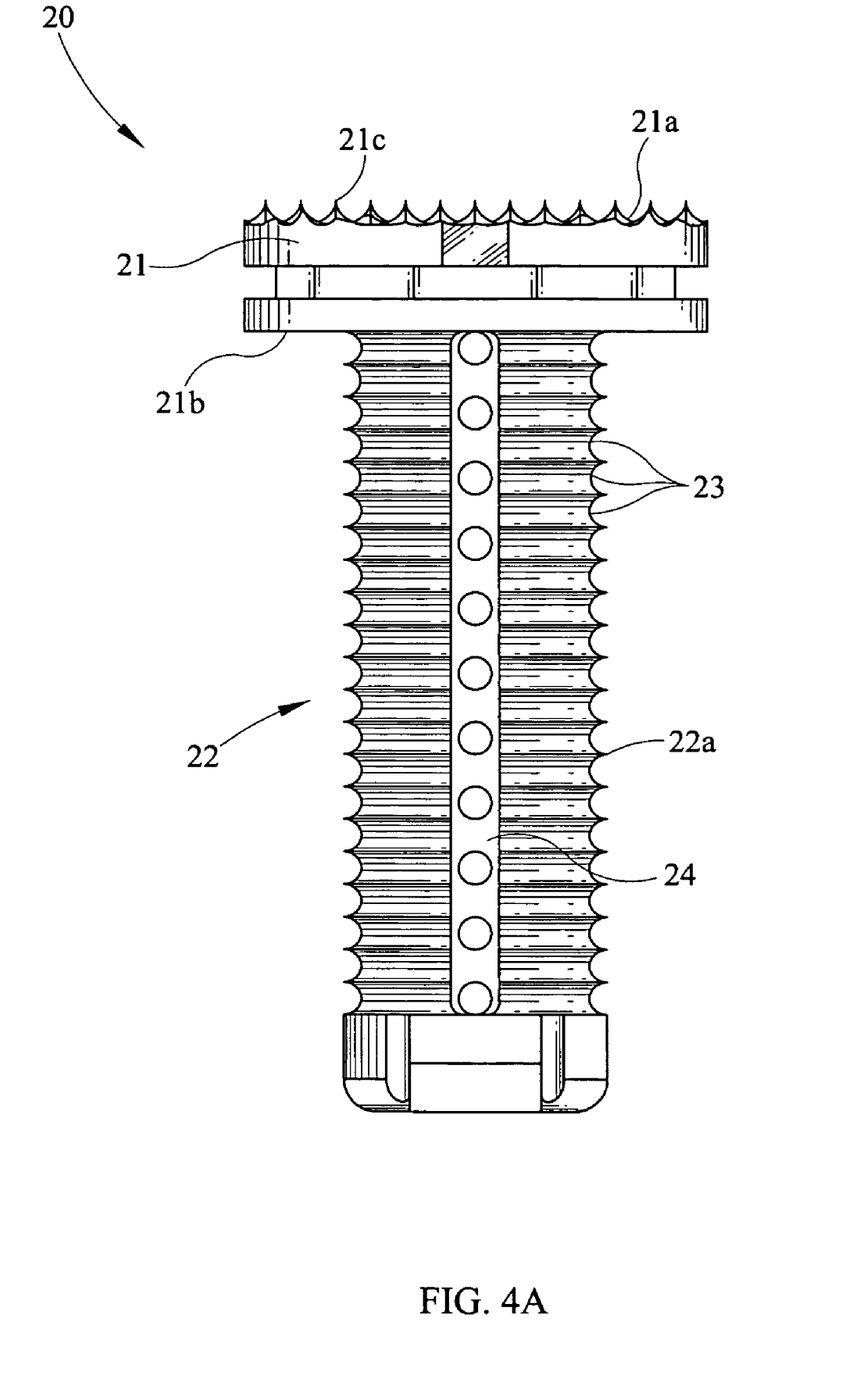
FIG. 4(A) is a side view depicting the inner member of one embodiment of the present invention.
Figure 4B:
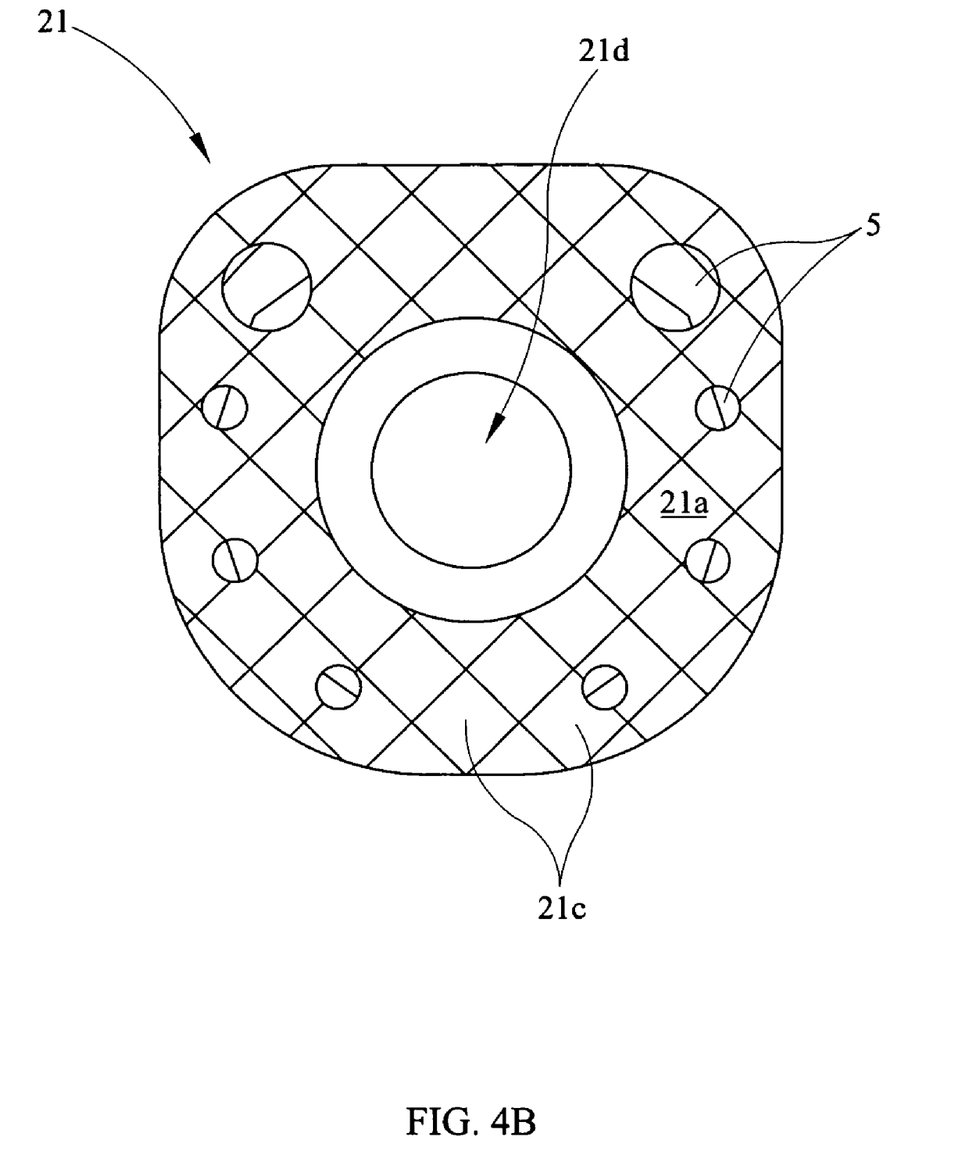
FIG. 4(B) is a top view depicting the first endplate of one embodiment of the present invention.
Figure 7:
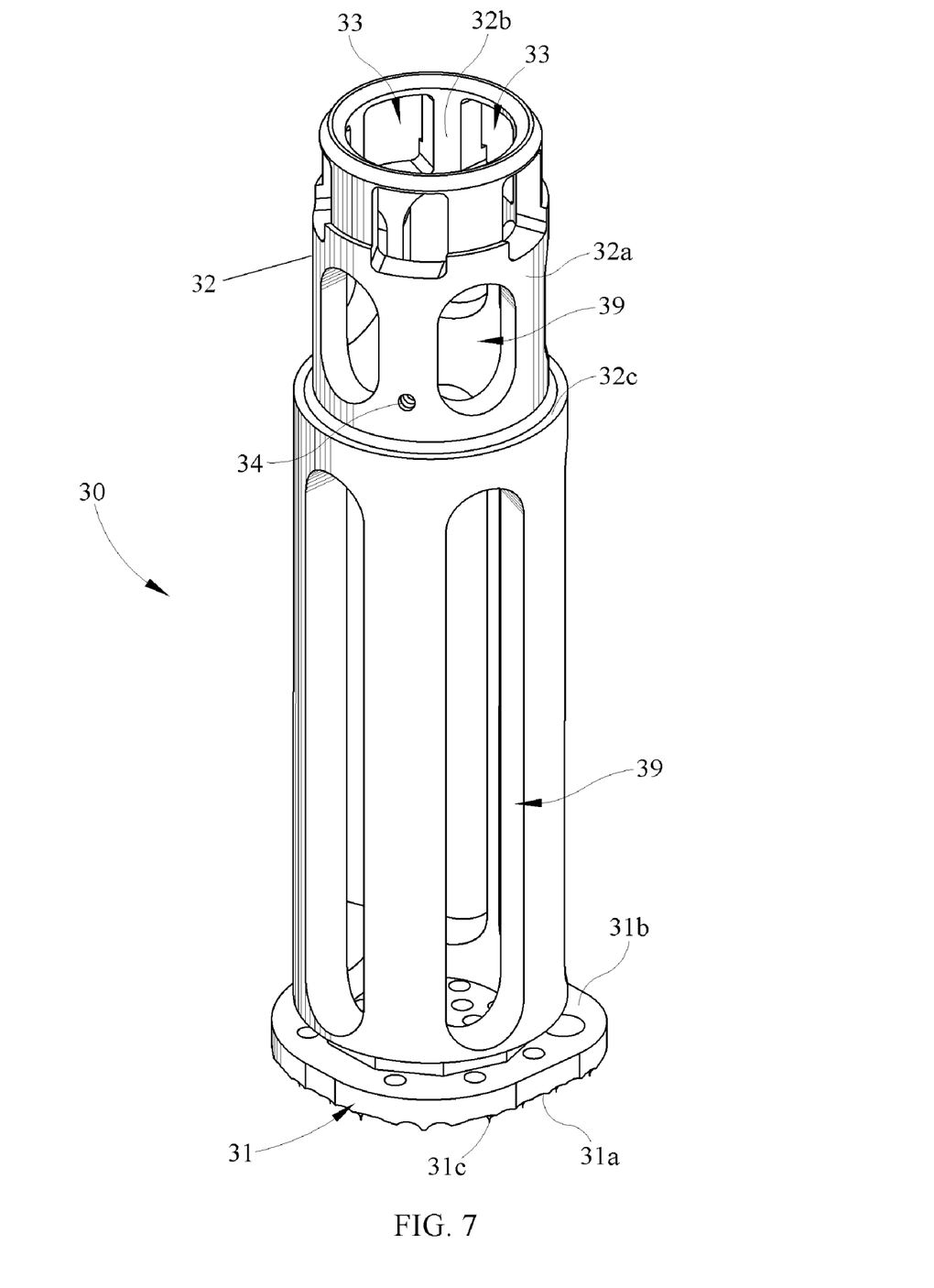
FIG. 7 is a perspective view depicting an outer cage of one embodiment of the present invention.

FIG. 1 shows an embodiment with a short outer cage 30. FIGS. 2 and 7 show a second embodiment with a longer outer cage 30. Referring now to FIGS. 4, 4A, and 4B, the apparatus 10 comprises an inner member 20; an outer cage 30; a finger cage 40; and a lock ring 50. In the embodiment shown, the inner member 20 includes a first endplate 21 that serves as the uppermost surface of the prosthesis and fits against the healthy vertebra adjacent to the uppermost removed bone. The first endplate 21 includes an upper surface 21a and a lower surface 21b. The upper surface 21a of the first endplate 21 may include spikes 21c, ridges, or some other protrusion or surface treatment in order to facilitate fusion between the prosthesis and the adjacent bone, thus providing better fixation of the prosthesis and increasing the life of the implant. In other embodiments, the first endplate 21 also can include an aperture 21d, preferably located at or near the center of the first endplate 21. In one embodiment, a cupped insert (not shown) is placed in the aperture 21d. The purpose of the aperture 21d, and the cupped insert, will be explained below.

Referring now to FIG. 7, the outer cage 30 includes a second endplate 31 that serves as the lowermost surface of the prosthesis and fits against the healthy vertebra adjacent to the lowermost removed bone. The second endplate 31 includes a lower surface 31a and an upper surface 31b. The lower surface 31a of the second endplate 31 may include spikes 31c, ridges, or some other protrusion or surface treatment in order to facilitate fusion between the prosthesis and the adjacent bone, thus providing better fixation of the prosthesis and increasing the life of the implant. The second endplate 31 also can include an aperture (not shown), preferably located at or near the center of the second endplate 31.

As can be seen in FIG. 4, the inner member 20 further comprises a hollow inner sleeve 22 that depends distally in the longitudinal direction from the lower surface 21b of first endplate 21. The inner sleeve 22 has an outer surface 22a that includes a number of circumferential grooves 23. Preferably, the grooves are separated by thin ridges and are approximately one (1) millimeter wide, though many spacings and numbers are possible. The inner sleeve 22 further comprises a number of slots 24 that are spaced longitudinally along the outer surface 22a of the inner sleeve 22.

Referring again to FIG. 7, the outer cage 30 further comprises a hollow outer sleeve 32 depending distally in the longitudinal direction from the upper surface 31b of second endplate endplate 31. The outer sleeve has an outer surface 32a and an inner surface 32b. The perimeter of the inner surface 32b of outer sleeve 32 is designed such that the inner sleeve 22 can fit within the outer sleeve 32. When the inner sleeve 22 is in place within the outer sleeve 32, it is free to slide axially relative to the outer sleeve 32. The outer sleeve 32 also includes locking apertures 33 that allow access to grooves of inner sleeve 22 when inner sleeve 22 is in place within the outer sleeve 32.

Figure 3:
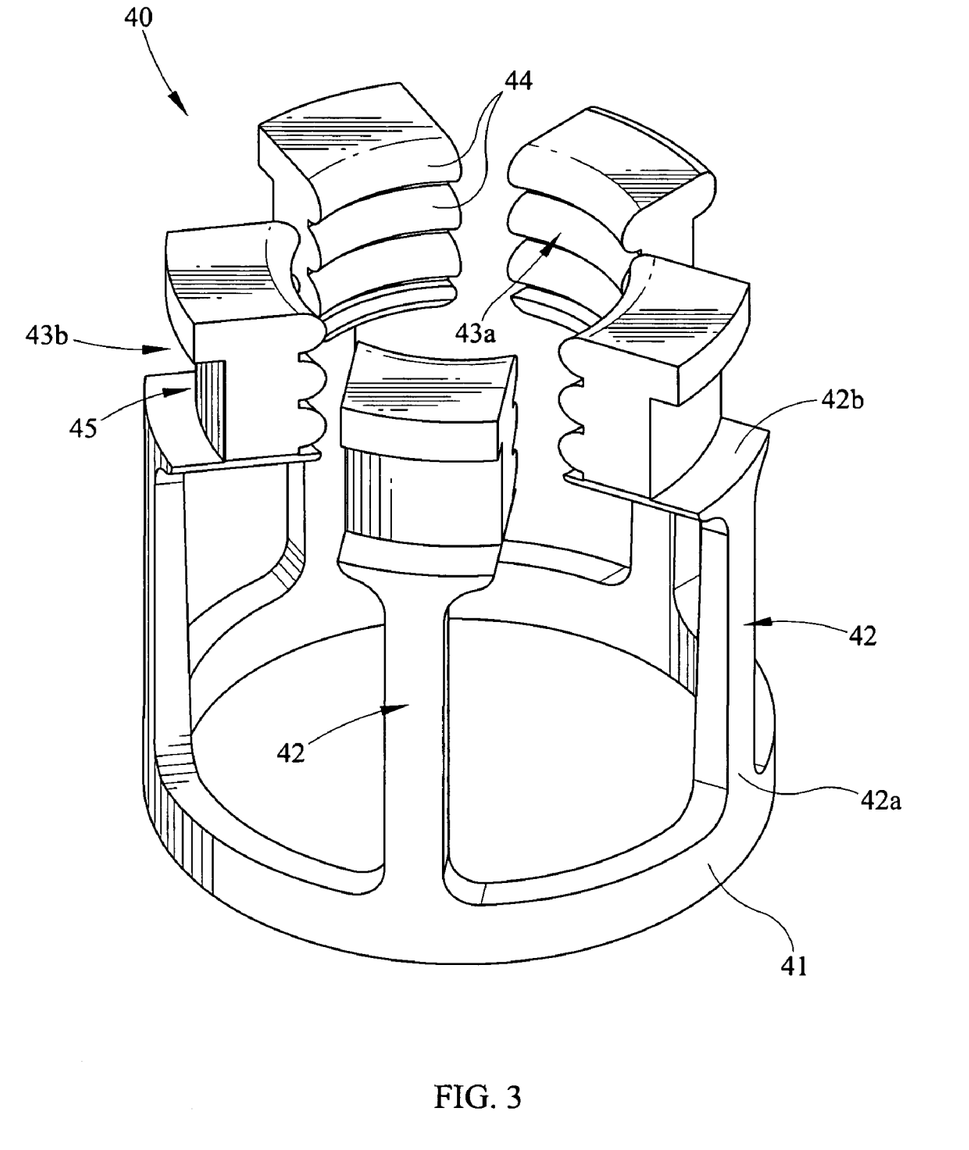
FIG. 3 is a partial perspective view of a finger cage of one embodiment of the present invention.

As shown in FIG. 3, the finger cage 40 includes a ring 41 that fits over the outer sleeve 32 and rests on a ledge 31f that is formed at the intersection of the outer sleeve 32 and the second endplate 31. Depending distally in a longitudinal direction from the ring 41 are one or more fingers 42. Preferably, there are a plurality of fingers 42. Each of the fingers 42 has a first end 42a and a second end 42b. The first end 42a is the point of attachment with the ring 41. The fingers 42 are preferably resilient, allowing the second end 42b to bend inward under force toward the center of the ring 41 while maintaining the capability to return to their original position after the force is removed from the finger 42. Preferably, the fingers 42 are resiliently biased outwardly.

Each of the fingers 42 has a tab 43 at its second end 42b. Each tab 43 has an interior side 43a and an exterior side 43b. The interior side 43a of each tab 43 has incrementally spaced male nubs 44. Each of the exterior sides 43b of tabs 43 have locking grooves 45.

When the ring 41 of the finger cage 40 is in place on the ledge 31f of the outer cage, the tabs 43 of the fingers 42 align with locking apertures 33 of the outer sleeve 32. In resting position, with no force applied to the fingers 42, the tabs 43 are located within the apertures 33, but are not forced to engage the circumferential grooves 23 of the inner sleeve 22. However, when inwardly-directed force is applied to the tabs 43 of fingers 42, the tabs 43 push through the locking apertures 33 of the outer sleeve 32 and the male nubs 44 of tabs 43 meshingly engage with the grooves 23 of the inner sleeve 22. When the male nubs 44 of finger cage 40 engage the grooves 23 of the inner sleeve 22, the inner sleeve 22 is locked in place within the outer sleeve 32, and the height 100 of the apparatus 10 is fixed.

Figure 5:
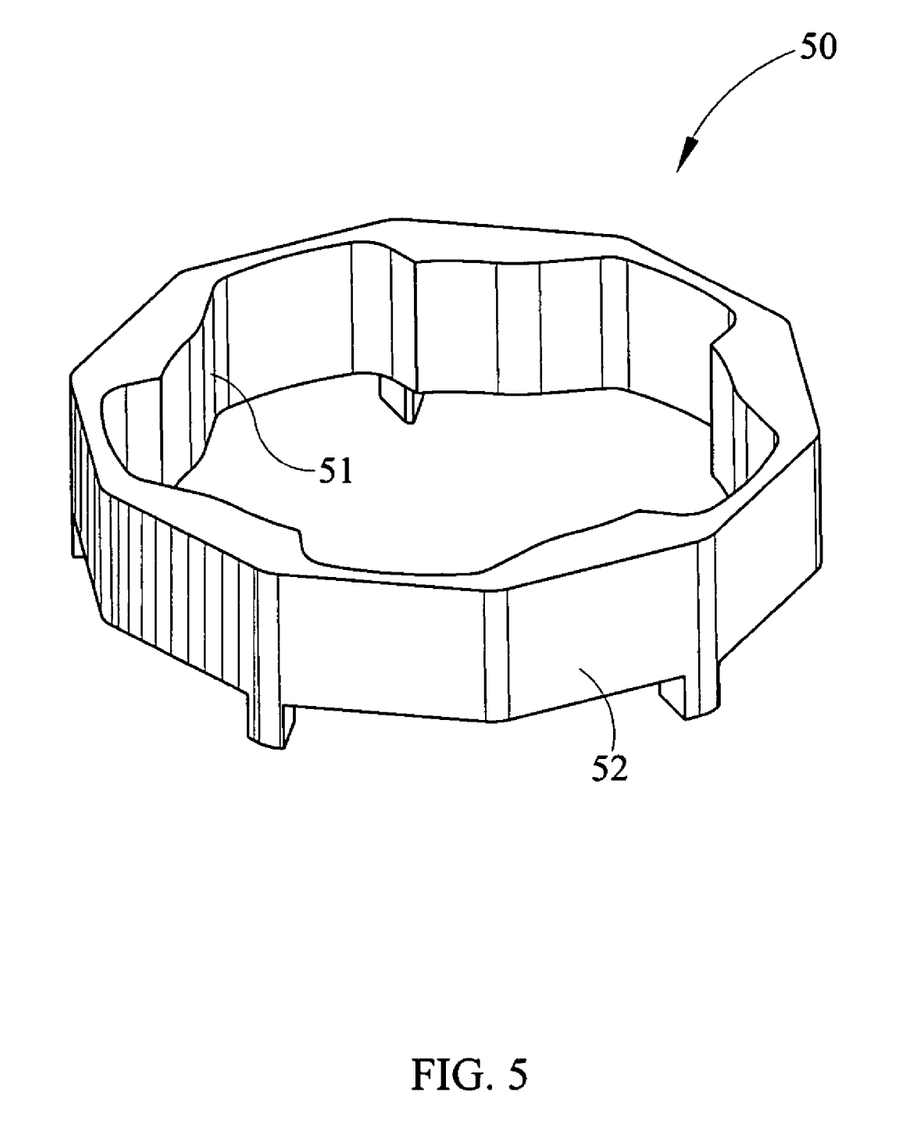
FIG. 5 is a partial perspective view depicting a locking ring of one embodiment of the present invention.
Figure 6:
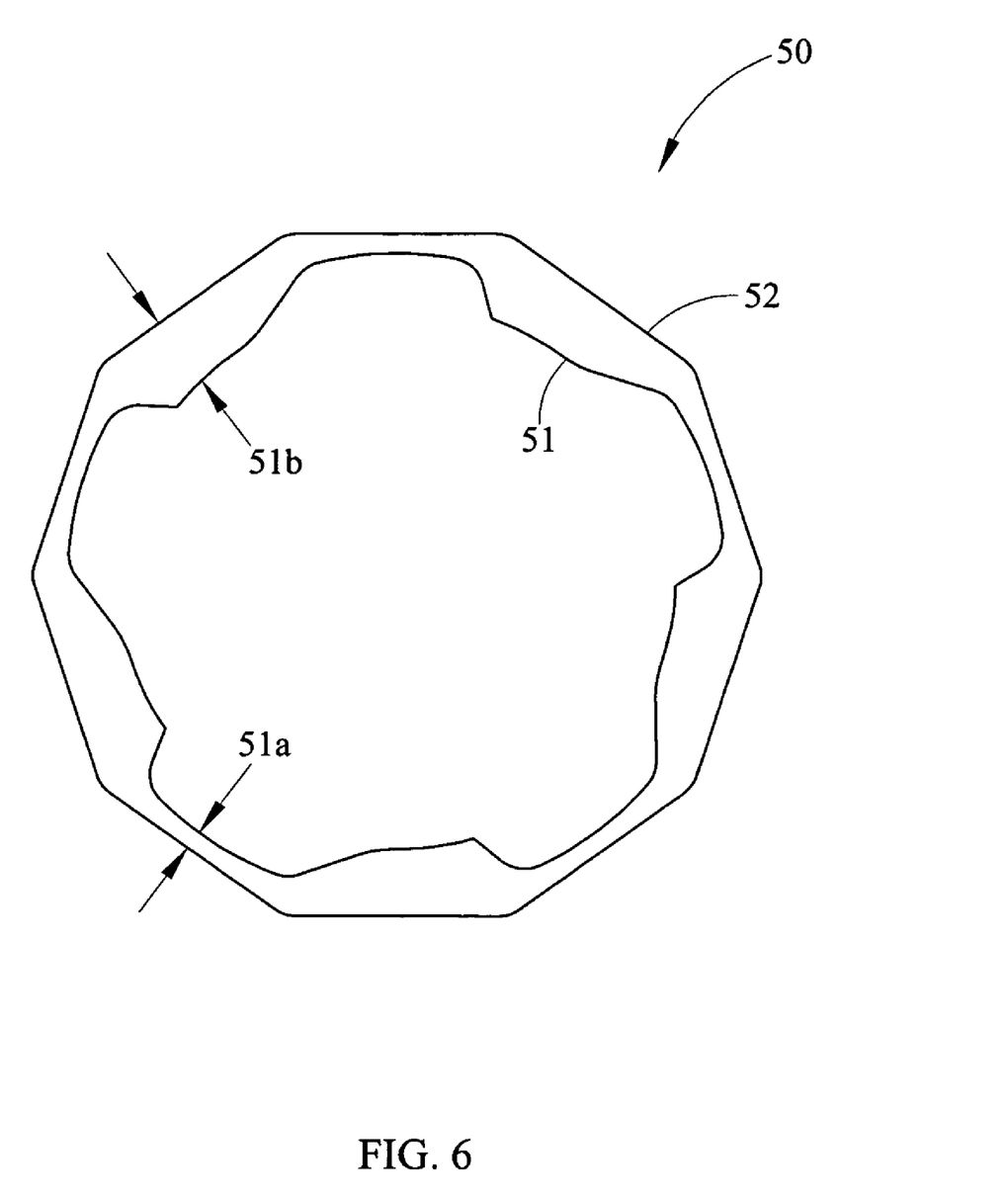
FIG. 6 is a top view depicting the locking ring shown in FIG. 5.

To effectuate the locking action, the apparatus 10 includes a locking ring 50 (see FIGS. 5 and 6). The locking ring 50 fits over the second end 42b of fingers 42 such that it fits within the locking grooves 45 located on the exterior side 43b of tabs 43. The locking ring 50 rotates about the grooves 45 about the longitudinal axis of the apparatus 10. Preferably, the locking ring 50 is rotatable between two positions—locked and unlocked.

The locking ring 50 has an interior surface 51 and an exterior surface 52. The interior surface 51 is in contact with the locking groove 45 of the tabs 43. The interior surface 51 of locking ring 50 is cammed such that the thickness of the locking ring 50 varies over the course of its circumference in a manner allowing the locking ring to be rotated relative to the finger cage 40 between a first locked position and a second unlocked position. Referring to FIG. 6, when the locking ring is in a first position within the locking groove 45 of the finger cage 40, a thinner portion 51a of the locking ring 50 is in contact with each of the locking grooves 45 of the exterior side 43b of tabs 43. In this position, the locking ring does not apply inwardly-directed force to the fingers 42. Therefore, the male nubs 44 of tabs 43 do not mesh with the grooves 23 of the inner sleeve 22. Conversely, when the locking ring is rotated to a second position, a thicker portion 51b of the locking ring 50 is in contact with each of the locking grooves 45 of the exterior side 43b of tabs 43. In the second position, the locking ring 50 squeezes the resilient fingers 42 inward, bringing the male nubs 44 of tabs 43 into contact with the grooves 23 of the inner sleeve 22. When the locking ring 50 is in the second, or locked, position, the inner sleeve 22 cannot slide axially relative to the outer sleeve 32. Therefore, the height 100 of the apparatus 10 is fixed.

It is also possible to include a secondary locking mechanism, such as a locking screw (not shown), that prevents rotation of the inner sleeve 22 within the outer sleeve 32 after the desired height 100 of the apparatus 10 is determined and the locking ring 50 is rotated to the second, or locked, position. In one embodiment, the outer sleeve 32 may include one or more locking apertures 34. Once the locking ring 50 is rotated to the locked position, the inner sleeve 22 is rotated within the outer sleeve 32 such that the locking aperture 34 of the outer sleeve 30 is aligned with one of the slots 24 and can receive a screw in one of the holes therein. In another embodiment, the slots 24 of the inner sleeve 22 can align with one or more appurtenances in the inner surface 32b so that the appurtenances ride in the slots 24 and prevent rotation.

In another embodiment, shown in FIG. 2, the ring 41 of the finger cage 40 does not rest on a ledge 31f formed at the intersection of the second endplate 31 and the outer sleeve 32, but instead on a plateau 32c that is located on the outer surface 32a of outer sleeve 32 (see FIG. 7). Below the plateau 32c, the outer sleeve 32 extends distally in the longitudinal direction to second endplate 31. The same finger cage 40 and inner member 20 are used in this embodiment. This embodiment is preferred when it is necessary for the apparatus 10 to replace a large amount of bone because the elongated outer sleeve 32 allows for a significantly taller prosthesis with which the components of the shorter apparatus 10 other than the outer sleeve 32, such as the finger cage 40 and the inner member 20, are still compatible.

Preferably, the first and second endplates 20, 30 include bone openings 5, allowing bone graft to be packed inside. This allows the bone graft to fuse to the prosthesis, then grow outward into the body after implantation and connect with the healthy bone adjacent to the prosthesis, improving fixation of the device within the body. The outer sleeve 40 and the inner sleeve 50 also preferably include openings 39 to allow more bone graft to be packed inside the hollow of the inner sleeve 50 such that it can grow out of the slots and fuse with adjacent bone. Further, as mentioned above, the first endplate 21 includes an aperture 21d, while the second endplate 31 can include an aperture. The aperture 21d of the first endplate 21 and the aperture of the second endplate 31, respectively, align with the hollow sections of the inner and outer sleeves 22, 32, respectively. This allows bone graft to be packed inside the hollow sections of the inner and outer sleeves 22, 32 and grow out of the apertures 21d, to fuse with the healthy bone adjacent the apparatus 10. Further, cupped inserts (not shown) can be placed within the aperture 21d of the first endplate 21 and the aperture of the second endplate 31, respectively. Bone graft can be placed in the cupped inserts, ensuring that bone graft will be in contact with the adjacent healthy bone even if the device is expanded after the bone graft is packed into the hollow sections of the inner and outer sleeves 22, 32. The cupped inserts are preferably slotted, thus still allowing bone graft to be packed in the hollow sections of the inner and outer sleeves 22, 32 and grow through the cupped inserts to fuse with the healthy bone. Also, although it is not required, it is preferred that the prosthesis be made of titanium alloy, such as Ti-4Al-6Va.

The apparatus 10 is manufactured of materials that are suitable for implantation in the human body. Many such materials are known presently. In the preferred embodiment, the apparatus 10 is made of titanium alloy, such as Ti-4Al-6Va.

While there has been described and illustrated particular embodiments of an adjustable corpectomy apparatus, it will be apparent to those skilled in the art that variations and modifications may be possible without deviating from the broad spirit and principle of the present invention, which shall be limited solely by the scope of the claims appended hereto which shall be limited solely by the scope of the claims appended hereto.

What is claimed is:

1. An adjustable corpectomy apparatus comprising:
   a first member comprising a first endplate and a shaft having circumferential grooves axially disposed about an external surface thereof;
   a second member comprising a cylindrical body for receiving said first member within an inner radial surface thereof and a second endplate adjacent said second member and having openings therethrough at spaced intervals therearound;
   a set of fingers extending in a longitudinal direction from a ring-like base on said second member and having internal surfaces and external surfaces, a proximal end, and a distal end and having a locking groove disposed about said external surfaces, wherein said internal surfaces of said set of fingers are disposed radially outwardly of said first member and are radially aligned with said external surface of said first member; and
   a non-threaded locking ring disposed externally of said set of fingers having an external surface and an internal surface wherein said internal surface resides about said locking groove.

2. The adjustable corpectomy apparatus of claim 1 wherein said shaft of said first member further comprises openings therein to facilitate bone graft ingrowth.

3. The adjustable corpectomy apparatus of claim 2 wherein said first endplate further comprises apertures therein to facilitate bone graft ingrowth.

4. The adjustable corpectomy apparatus of claim 1 wherein said second member further comprises apertures therein to facilitate bone graft ingrowth.

5. The adjustable corpectomy apparatus of claim 4 wherein said second endplate further comprises apertures therein to facilitate bone graft ingrowth.

6. The adjustable corpectomy apparatus of claim 1 wherein said adjustable corpectomy apparatus is made from a titanium alloy.

7. The adjustable corpectomy apparatus of claim 1 wherein said first endplate further comprises a surface to facilitate fusion with a first vertebra.

8. The adjustable corpectomy apparatus of claim 1 wherein said second endplate further comprises a surface to facilitate fusion with a second vertebra.

9. The adjustable corpectomy apparatus of claim 1 wherein said distal end of said set of fingers further comprises at least one nub protruding therefrom for engaging said circumferential grooves of said first member.

10. The adjustable corpectomy apparatus of claim 9 wherein said distal end of said set of fingers resides in said openings in said cylindrical body of said second member.

11. The adjustable corpectomy apparatus of claim 10 wherein said locking ring is rotatable from a first, unlocked position to a second, locked position.

12. The adjustable corpectomy apparatus of claim 11 wherein said locking ring further comprises circumferentially alternating regions of thick sections and thin sections, connected by camming surfaces.

13. The adjustable corpectomy apparatus of claim 12 wherein when said locking ring is in said first position, said thin section resides about said groove.

14. The adjustable corpectomy apparatus of claim 13 wherein when said locking ring is rotated to a rotated position toward said second position, said camming surfaces is in contact with said groove, forcing said distal ends of said set of fingers radially inwardly through said openings in said second member and is in engagement with selected grooves of said first member.

15. The adjustable corpectomy apparatus of claim 14 wherein when said locking ring is rotated fully to its second position, said thick section of said locking ring resides in said groove of said set of fingers, thus being fully engaged with said distal ends of said fingers in said groove of said first member, thus locking the apparatus height.

16. An adjustable corpectomy apparatus comprising:
   a first endplate coupled to a longitudinal member, said longitudinal member having circumferentially disposed grooves axially aligned on an outer surface thereof;
   a second endplate coupled to a cage member for receiving said longitudinal member therein, said cage member having at least one finger-receiving opening through a sidewall thereof;
   a set of fingers depending from a ring-like base in a longitudinal direction and having an external facing groove thereon for receiving a locking ring, said set of fingers having at least one protrusion thereon for engaging said grooves on said outer surface of said longitudinal member;
   a non-threaded annular locking ring disposed around said external facing groove of said set of fingers and having an internal surface comprising a thin wall and a thick wall separated by a camming surface; and
   wherein as said annular locking ring is in a rotated position from a first position toward a second position, said internal surface is pressed against said external-facing groove of said set of fingers, forcing said fingers radially inward to engage said grooves on said outer surface of said longitudinal member.

* * * * *